US010070967B2

(12) United States Patent
Chavarria et al.

(10) Patent No.: US 10,070,967 B2
(45) Date of Patent: Sep. 11, 2018

(54) ORTHOPAEDIC IMPLANT AND METHOD OF INSTALLING SAME

(71) Applicant: DEPUY SYNTHES PRODUCTS, INC., Raynham, MA (US)

(72) Inventors: Jason M. Chavarria, Warsaw, IN (US); Sarah M. Anthony, Leesburg, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/426,661

(22) Filed: Feb. 7, 2017

(65) Prior Publication Data
US 2017/0143498 A1    May 25, 2017

Related U.S. Application Data

(62) Division of application No. 14/606,111, filed on Jan. 27, 2015, now Pat. No. 9,561,109, which is a division
(Continued)

(51) Int. Cl.
*A61F 2/40* (2006.01)
*A61F 2/28* (2006.01)
(Continued)

(52) U.S. Cl.
CPC ........ *A61F 2/4014* (2013.01); *A61B 17/8057* (2013.01); *A61B 17/8061* (2013.01); *A61B 17/8605* (2013.01); *A61B 17/8625* (2013.01); *A61F 2/30749* (2013.01); *A61F 2/4003* (2013.01); *A61F 2002/30332* (2013.01);
(Continued)

(58) Field of Classification Search
CPC ...... A61F 2/38; A61F 2/34; A61F 2/36; A61F 2/40
See application file for complete search history.

(56) References Cited

U.S. PATENT DOCUMENTS 2,381,050 A    8/1945 Hardinge
2,397,545 A    4/1946 Hardinge
(Continued)

FOREIGN PATENT DOCUMENTS

DE         10123517 C1    11/2002
DE      102006047663 A1     4/2008
(Continued)

OTHER PUBLICATIONS

PCT International Search Report and Written Opinion, International Application No. PCT/EP2012/052463 dated Mar. 23, 2012.
(Continued)

*Primary Examiner* — Jason-Dennis Stewart
(74) *Attorney, Agent, or Firm* — Barnes & Thornburg, LLP

(57) ABSTRACT

An orthopedic implant comprises an articulation head comprising a bearing surface and a reverse surface and a securement disk. The securement disk comprises an attachment surface attached to at least a portion of the reverse surface of the articulation head, a securement surface opposite the attachment surface and adapted for coupling to a fixation plate secured to a bone, and at least one opening formed in the securement surface of the securement disk and adapted to accept fasteners therein. The securement disk comprises a porous material.

5 Claims, 7 Drawing Sheets

Related U.S. Application Data of application No. 13/800,149, filed on Mar. 13, 2013, now Pat. No. 8,968,409.

(51) Int. Cl.
*A61F 2/30* (2006.01)
*A61B 17/80* (2006.01)
*A61B 17/86* (2006.01)

(52) U.S. Cl.
CPC ............ *A61F 2002/30433* (2013.01); *A61F 2002/30777* (2013.01); *A61F 2002/30787* (2013.01); *A61F 2002/4007* (2013.01)

(56) References Cited

U.S. PATENT DOCUMENTS

| | | |
|---|---|---|
| 2,612,159 A | 9/1952 | Collison |
| 3,374,786 A | 3/1968 | Callender, Jr. |
| 3,554,193 A | 1/1971 | Konstantinou et al. |
| 4,005,495 A | 2/1977 | Locke et al. |
| 4,045,825 A | 9/1977 | Stroot |
| 4,101,985 A | 7/1978 | Baumann et al. |
| 4,129,903 A | 12/1978 | Huggler et al. |
| 4,438,762 A | 3/1984 | Kyle et al. |
| 4,612,920 A | 9/1986 | Lower et al. |
| 4,657,001 A | 4/1987 | Fixel |
| 4,686,971 A | 8/1987 | Harris et al. |
| 4,776,329 A | 10/1988 | Treharne |
| 4,791,918 A | 12/1988 | Von Hasselbach |
| 4,795,473 A | 1/1989 | Grimes |
| 4,904,264 A | 2/1990 | Scheunemann et al. |
| 4,976,740 A | 12/1990 | Kleiner et al. |
| 4,998,937 A | 3/1991 | Grimes |
| 5,087,260 A | 2/1992 | Fixel |
| 5,197,989 A | 3/1993 | Hinckfuss et al. |
| 5,376,125 A | 12/1994 | Winkler et al. |
| 5,376,126 A | 12/1994 | Lin |
| 5,569,263 A | 10/1996 | Hein et al. |
| 5,645,607 A | 7/1997 | Hickey et al. |
| 5,658,339 A | 8/1997 | Tronzo et al. |
| 5,725,597 A | 3/1998 | Hwang et al. |
| 5,733,292 A | 3/1998 | Gustilo et al. |
| 5,766,263 A | 6/1998 | Grundei et al. |
| 5,800,553 A | 9/1998 | Albrektsson et al. |
| 5,800,554 A | 9/1998 | Scholz et al. |
| 5,800,557 A | 9/1998 | Elhami et al. |
| 6,139,552 A | 10/2000 | Horiuchi et al. |
| 6,228,120 B1 | 5/2001 | Leonard et al. |
| 6,375,684 B1 | 4/2002 | Kriek |
| 7,097,663 B1 | 8/2006 | Nicol et al. |
| 7,135,023 B2 | 11/2006 | Watkins et al. |
| 7,425,214 B1 | 9/2008 | McCarthy et al. |
| 8,092,466 B2 | 1/2012 | Splieth et al. |
| RE43,482 E | 6/2012 | Mikol et al. |
| 8,968,409 B2 | 3/2015 | Chavarria et al. |
| 9,561,109 B2 | 2/2017 | Chavarria et al. |
| 2002/0107520 A1 | 8/2002 | Hoffman |
| 2002/0193797 A1 | 12/2002 | Johnson et al. |
| 2003/0028253 A1 | 2/2003 | Stone et al. |
| 2003/0069582 A1 | 4/2003 | Culbert |
| 2003/0187512 A1 | 10/2003 | Frederick et al. |
| 2005/0197712 A1 | 9/2005 | Bigsby et al. |
| 2006/0009852 A1 | 1/2006 | Winslow et al. |
| 2006/0116679 A1 | 6/2006 | Lutz et al. |
| 2006/0200249 A1 | 9/2006 | Beguin et al. |
| 2006/0217720 A1 | 9/2006 | Chieng |
| 2008/0177395 A1 | 7/2008 | Stinnette |
| 2010/0023131 A1 | 1/2010 | Crofford et al. |
| 2010/0331990 A1 | 12/2010 | Mroczkowski et al. |
| 2013/0035761 A1 | 2/2013 | Sharkey et al. |
| 2013/0197652 A1 | 8/2013 | Ekelund et al. |
| 2013/0338780 A1 | 12/2013 | Berchoux et al. |
| 2014/0094855 A1 | 4/2014 | Chavarria et al. |
| 2014/0114425 A1 | 4/2014 | Ekelund et al. |
| 2014/0121709 A1 | 5/2014 | Gonzalez-Hernandez |
| 2014/0121713 A1 | 5/2014 | Meulink et al. |
| 2015/0272643 A1 | 10/2015 | Berchoux et al. |

FOREIGN PATENT DOCUMENTS

| | | |
|---|---|---|
| DE | 102008053566 A1 | 6/2009 |
| EP | 1952788 A1 | 8/2008 |
| FR | 2946863 A1 | 12/2010 |
| GB | 2007980 A | 5/1979 |
| JP | 2004089712 A | 3/2004 |
| WO | 1985005027 A1 | 11/1985 |
| WO | 9739693 A1 | 10/1997 |
| WO | 2000009038 A2 | 2/2000 |
| WO | 2006126238 A2 | 11/2006 |
| WO | 2007024980 A2 | 3/2007 |
| WO | 2007082925 A2 | 7/2007 |
| WO | 2012104285 A1 | 8/2012 |
| WO | 2012130517 A1 | 10/2012 |

OTHER PUBLICATIONS

GB Search Report issued in connection to United Kingdom Application No. GB1105243.8 dated Jul. 17, 2011.

European Search Report for European Patent Application No. 14155805.6-1654 / 2792334, dated Sep. 24, 2014, 7 pages.

European Search Report for European Patent Application No. 15152190.3-1654, dated Apr. 24, 2015, 6 pages.

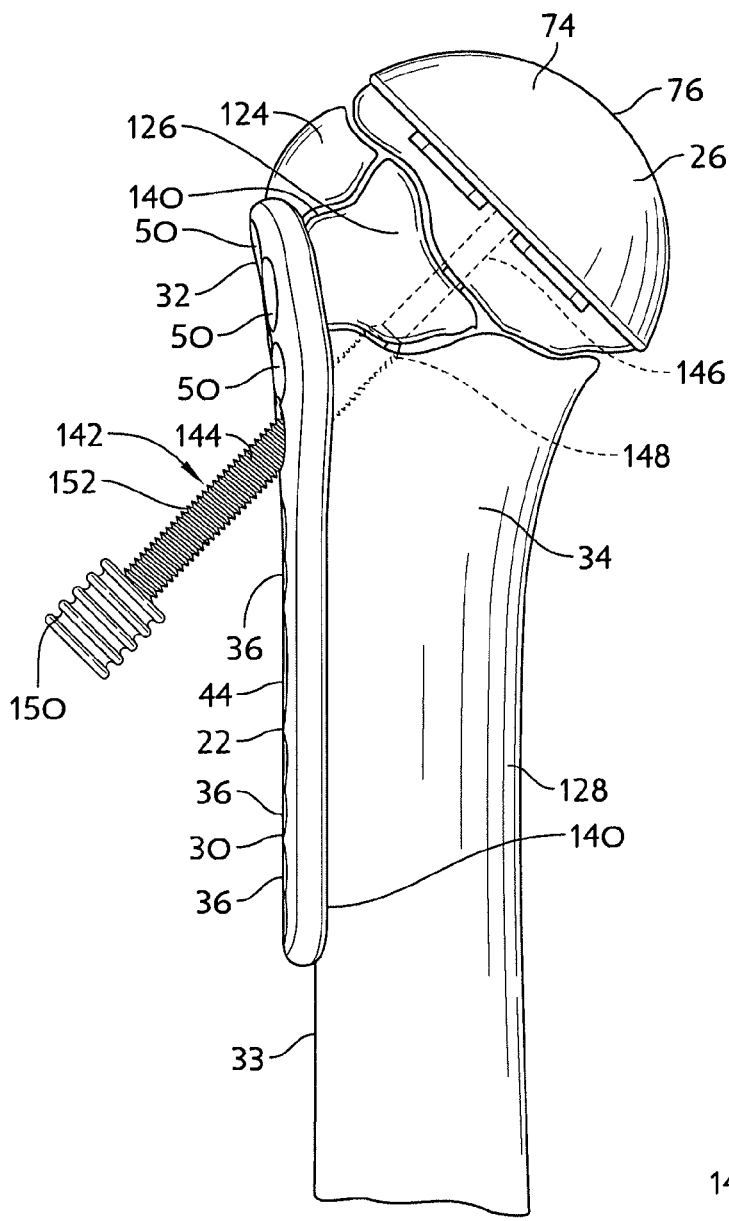
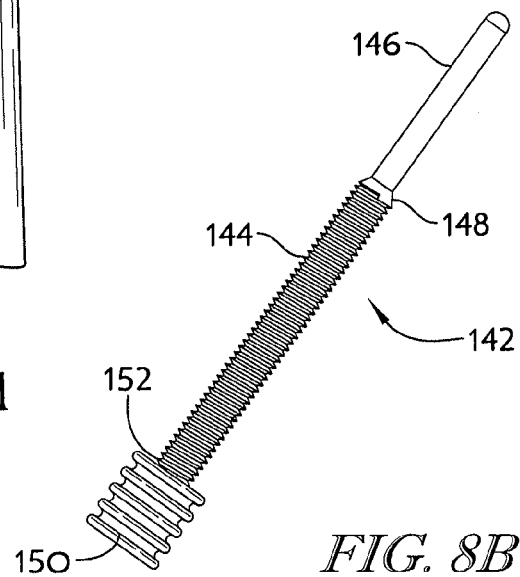
FIG. 8A
FIG. 8B

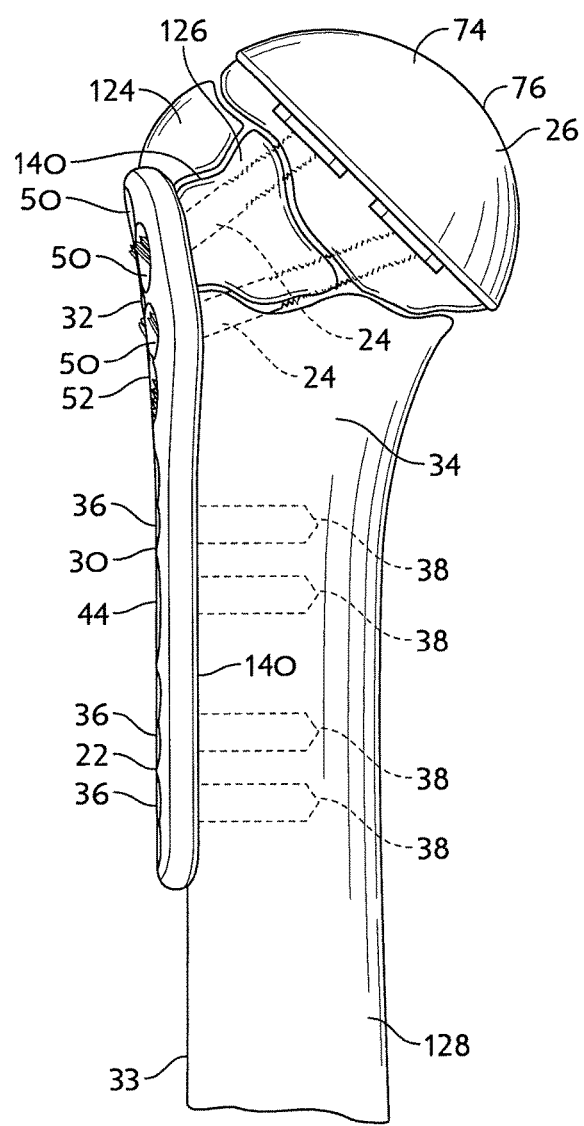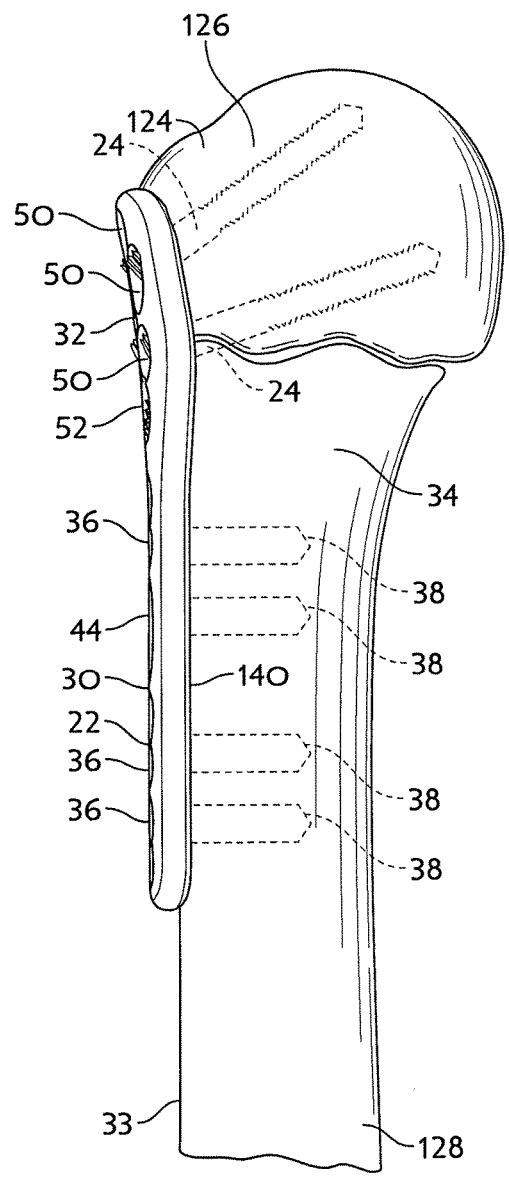
FIG. 9
FIG. 10

ORTHOPAEDIC IMPLANT AND METHOD OF INSTALLING SAME

CROSS REFERENCE TO RELATED APPLICATION

This application is a divisional of U.S. patent application Ser. No. 14/606,111, now U.S. Pat. No. 9,561,109, filed Jan. 27, 2015, which is a divisional of U.S. patent application Ser. No. 13/800,149, now U.S. Pat. No. 8,968,409, filed Mar. 13, 2013, the contents of each of which are incorporated herein by reference.

TECHNICAL FIELD

The present disclosure relates generally to orthopaedic implants, and more particularly, to orthopaedic implants for repairing and/or replacing natural joints.

BACKGROUND

A natural joint may undergo degenerative changes for a variety or reasons, for instance arthritis. Alternatively, a joint may be sufficiently fractured or otherwise damaged by an external force. When a joint is sufficiently degenerated or damaged, it may be necessary to replace a natural joint or portions of a natural joint with a prosthetic joint or portions of a prosthetic joint.

One such natural joint that may need replacement is the shoulder joint. Conventional shoulder prostheses comprise a humeral implant and optionally a glenoid implant. Typically, the humeral implant comprises a stem for insertion into a bore extending into the intramedullary canal generally along the longitudinal axis of the bone and an articulation component, such as a convex bearing head. Typically, the articulation component is coupled to a neck portion of the stem, which extends from the intramedullary canal at an inclined angle relative to the longitudinal axis of a distal portion of the stem in order to recreate the arrangement of the natural joint.

SUMMARY

According to one aspect, an orthopaedic implant comprises a fixation plate and an articulation component comprising a bearing surface and an opposing securement surface formed of a porous material. The implant further includes at least one fastener extending through the fixation plate and secured within the porous material of the securement surface of the articulation component.

The articulation component may include an articulation head having a convex outer surface forming the articulation surface and a reverse surface opposite the convex outer surface. A securement disk having an attachment surface may be disposed adjacent the reverse surface of the articulation head.

The securement disk may include a securement surface and at least one radial slot formed in the securement surface and adapted to accept the at least one fastener.

A shorter fastener may be secured within the radial slot near an inner edge of the radial slot and a longer fastener may be secured within the radial slot near an outer edge of the radial slot, thereby allowing flexibility in the length of fasteners used with the articulation component.

The radial slot may extend into the securement disk between the securement surface and the attachment surface.

The radial slot may include at least one wall along extending outwardly from at least a portion of a perimeter of the slot, wherein the fastener may engage the at least one wall and a wall forming the slot to retain the fastener within the slot.

The implant may include a plurality of fasteners and a plurality of radial slots within the securement disk, wherein each of the plurality of fasteners is secured within a respective radial slot of the plurality of radial slots.

The securement disk may be formed of titanium foam.

According to another aspect, an orthopaedic implant includes an articulation head comprising a bearing surface and a reverse surface and a securement disk. The securement disk includes an attachment surface attached to at least a portion of the reverse surface of the articulation head and a securement surface opposite the attachment surface and adapted for coupling to a fixation plate secured to a bone. At least one opening is formed in the securement surface of the securement disk and adapted to accept fasteners therein. The securement disk comprises a porous material.

The at least one opening may be in the form of a radial slot formed in the securement surface and adapted to accept fasteners.

A shorter fastener may be secured within the radial slot near an inner edge of the slot and a longer fastener may be secured within the radial slot near an outer edge of the slot, thereby allowing flexibility in the length of fasteners used with the articulation component.

The radial slot may extend into the securement disk between the securement surface and the attachment surface.

The radial slot may include at least one wall along extending outwardly from at least a portion of a perimeter of the slot, wherein the fastener may engage the at least one wall and a wall forming the slot to retain the fasteners within the slot.

The securement disk may be formed of titanium foam.

According to yet another aspect, a method of installing an orthopaedic implant includes the step of selecting at least a fixation plate and a set of fasteners for a patient, wherein the fixation plate and the set of fasteners correspond to the natural anatomy of a patient. The method further includes the steps of accessing the fractured bone and assessing the extent of fracture of the bone. If the extent of the fracture is at a first level, the fixation plate, an articulation component selected based on the patient's natural anatomy, and the set of fasteners are utilized to replace a portion of the fractured bone. If the extent of the fracture is at a second level different than the first level, only the fixation plate and the set of fasteners are utilized to repair the fractured bone.

If the fracture is at the first level, the method may further include the steps of removing a head of the fractured bone and securing the fixation plate to a surface of the fractured bone. The method may further include the steps of positioning the articulation component in the place of the head, aligning the articulation component with the fixation plate, and inserting the fasteners through the fixation plate and the articulation component to secure the articulation component to the fixation plate.

The method may further include the steps of selecting a set of fasteners having a length and securing the set of fasteners in radial slots formed in the articulation component. The structure of the articulation component forming the radial slots may be formed of a porous material. The length of the set of fasteners and a placement of the fasteners within the radial slots may determine a neck length.

The aligning step may include the steps of inserting a first end of an instrument through a hole in the fixation plate and guiding the first end into a hole formed within the articulation component. These steps set a neck length between the fixation plate and the articulation component and prevent rotation of the articulation component during placement of the fasteners.

If the fracture is at the second level, the method may further include the steps of securing the fixation plate to the bone and inserting the fasteners through the fixation plate and into a fractured native articulation component to secure the fractured native articulation component to the fixation plate.

Other aspects and advantages of the present disclosure will become apparent upon consideration of the following drawings and detailed description, wherein similar structures have similar reference numbers.

BRIEF DESCRIPTION OF THE DRAWINGS

The detailed description particularly refers to the following figures, in which:

FIG. 8A is a side elevational view of the orthopaedic implant of FIG. 1 implanted within the proximal humerus of FIG. 7 and depicting a first end of an instrument extending through the fixation plate and a second end of the tool extending into the articulation component of FIGS. 1-3 to align the fixation plate and the articulation component during surgery;

FIG. 8B is a perspective view of the instrument depicted in FIG. 8A for aligning the fixation plate and the articulation component during surgery;

FIG. 9 is a side elevational view of the fixation plate, the fasteners, and the articulation component of the orthopaedic implant of FIGS. 1 and 2 implanted within the proximal humerus; and FIG. 10 is a side elevational view of the fixation plate and the fasteners of orthopaedic implant of FIGS. 1 and 2 implanted within the proximal humerus.

DETAILED DESCRIPTION OF THE DRAWINGS

Figure 1:
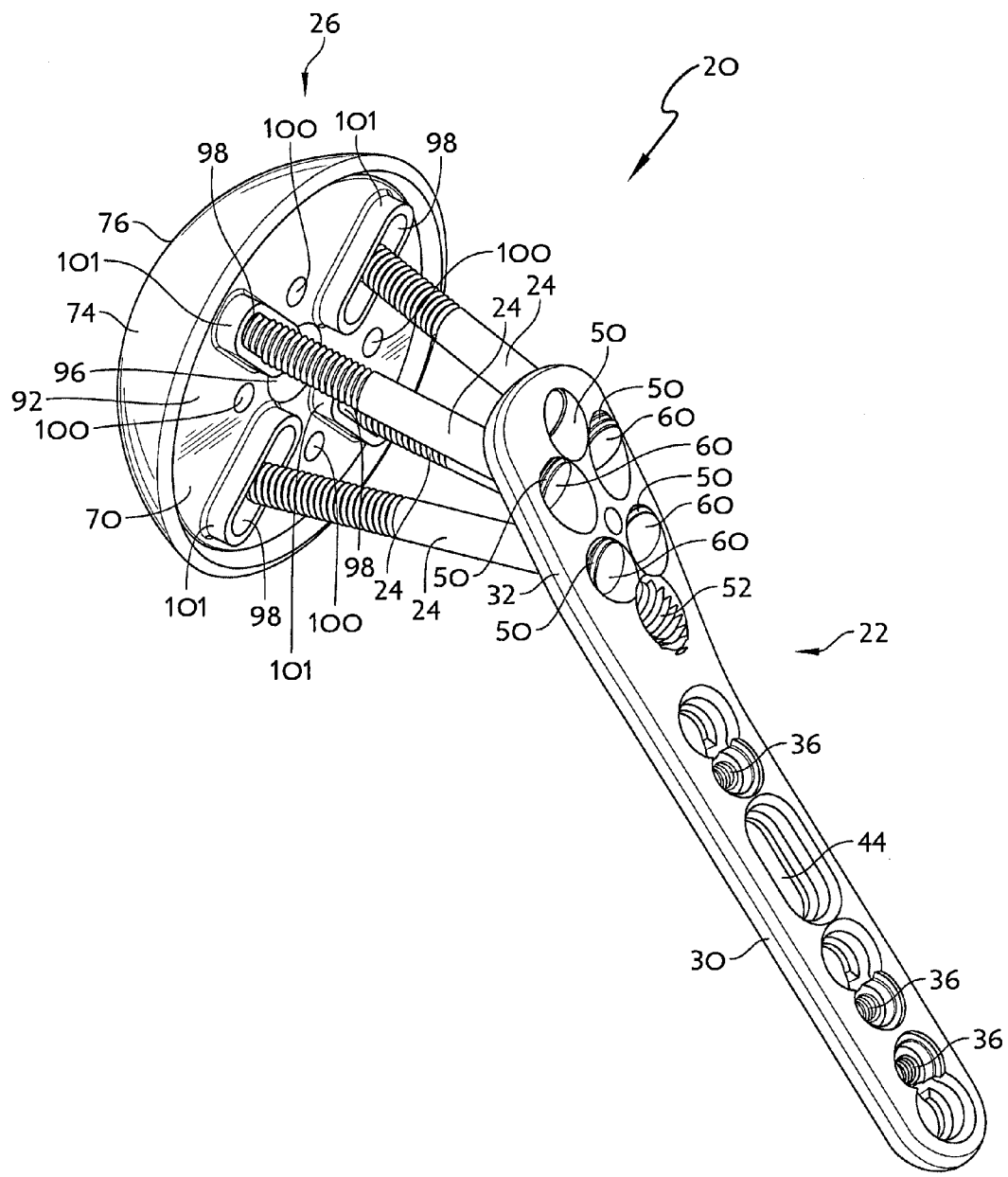
FIG. 1 is a top perspective view of a first embodiment of an orthopaedic implant, for example a humeral implant, including a fixation plate, an articulation component, and a plurality of fasteners for connecting the fixation plate and the articulation component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 2:
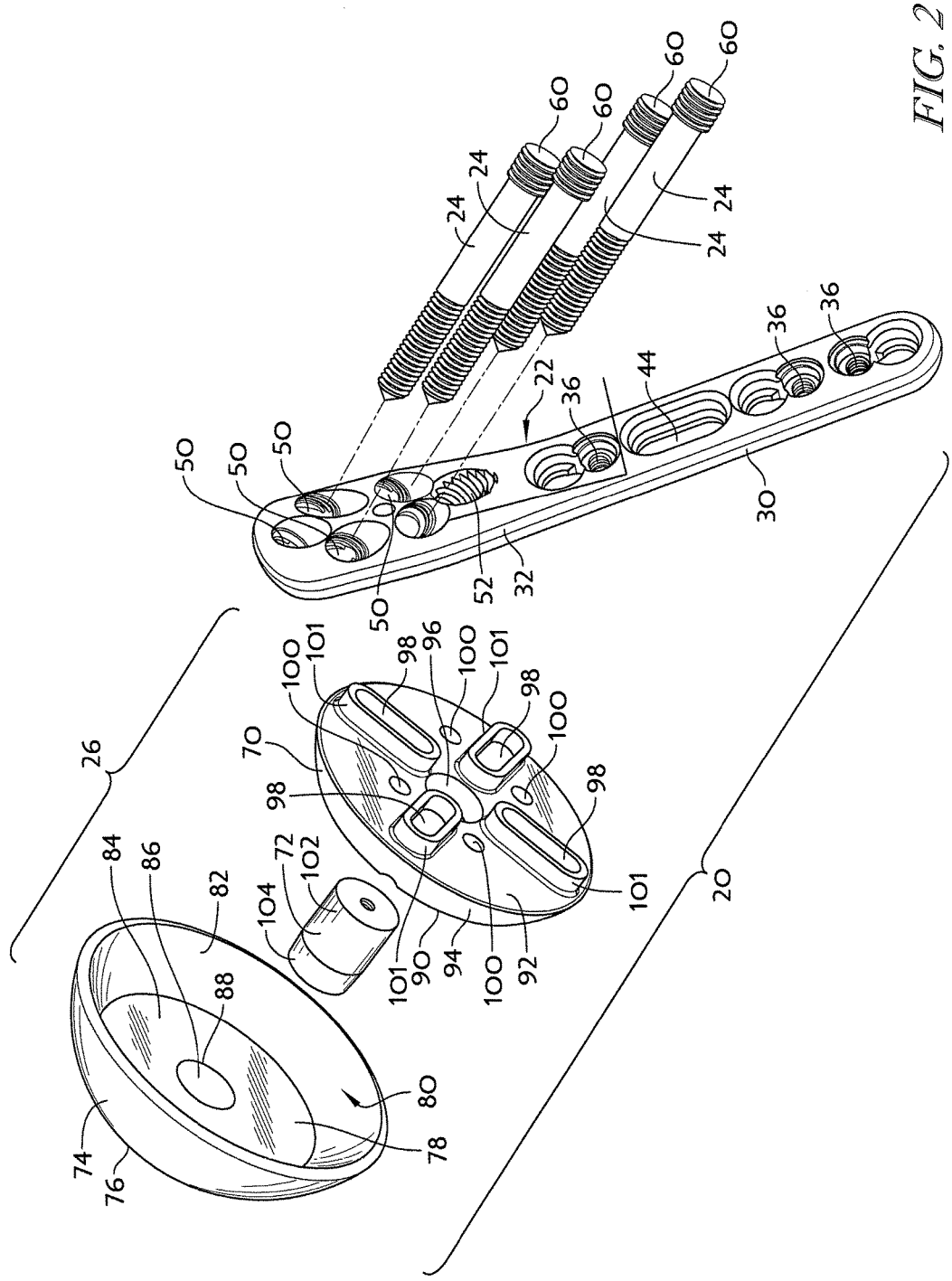
FIG. 2 is an exploded view of the arthroplasty implant of FIG. 1 and further depicting the articulation component including a securement disk, an articulation head, and a connector for joining the securement disk and the articulation head.

Referring now to the figures, an embodiment of an orthopaedic implant 20 is depicted in FIGS. 1 and 2. The orthopaedic implant 20 generally includes a fixation plate 22, a plurality of fasteners 24, for example screws, and an articulation component 26. The fixation plate 22 comprises an elongate body 30 and a head 32 arranged to conform to the surface of the lateral surface 33 of the proximal humerus 34. A plurality of screw holes 36 are formed within the body 30 for securing the fixation plate 22 to the proximal humerus 34 with bone screws 38, as shown in FIG. 9. While a particular number of screw holes 36 are depicted, any suitable number of screw holes 36 and corresponding bone screws 38 may be utilized to attach the fixation plate 22 to the proximal humerus 34. A slotted screw hole 44 is also provided for initial fixation of the fixation plate 22 to the proximal humerus 34. In particular, if utilized for initial fixation, a bone screw 38 may be inserted into the proximal humerus 34 through the slotted hole 44, allowing the fixation plate 22 to slide along the proximal humerus 34 before the fixation plate 22 is permanently attached.

Figures 4, 5:
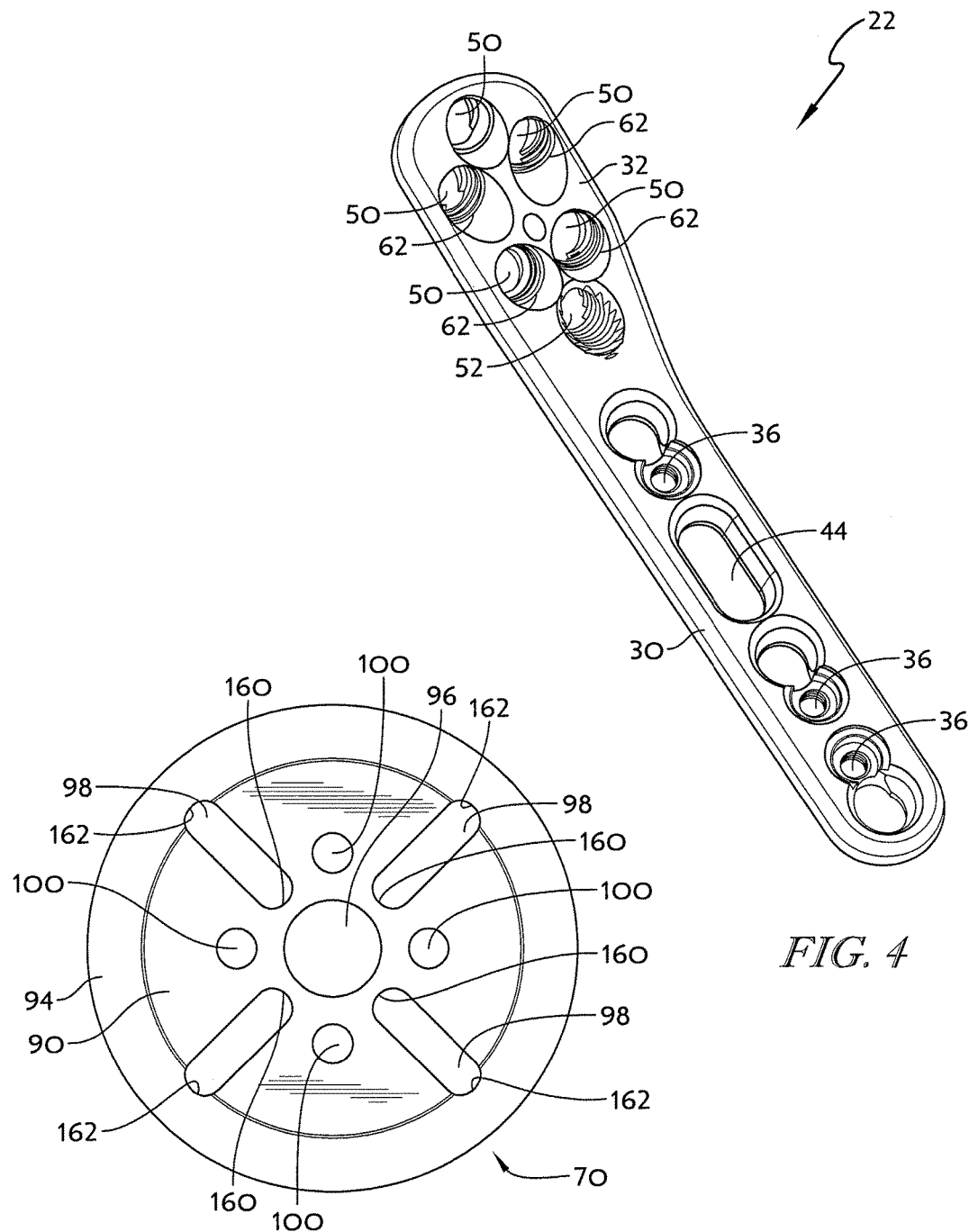
FIG. 4 is a perspective view of the fixation plate of FIG. 1.
FIGS. 5 and 6 are bottom and top elevational views of the securement disk of FIG. 2, wherein the securement disk includes a plurality of radial slots for accommodating the fasteners and a central circular hole for accommodating the connector of FIGS. 2 and 3.

Referring to FIGS. 1, 2, and 4, the head 32 of the fixation plate 22 extends from the body 30 and the head 32 tapers outwardly as it moves away from the body 30 to conform to the shape of the proximal humerus 34. The head 32 of the fixation plate 22 includes a number of screw holes 50 and a guide hole 52, wherein the screws 24 and/or an instrument 142, as described below, may be inserted through the screw holes 50 and the guide hole 52 to secure the fixation plate 22 to the articulation component 26 or a humeral head 120, as will be discussed in greater detail below. The guide hole 52 is disposed below the screw holes 50 and may be utilized in combination with an instrument 142 to align the fixation plate 22 with the articulation component 26, as will be discussed in greater detail hereinafter.

The screws 24 may be configured to be inserted into bone, titanium foam, and/or any other suitable material. The screws 24 include threading that is sized to mate with threading formed within the screw holes 50. Heads 60 of the screws have a diameter that is larger than the threading of the screws 24 and the screw holes 50. In this manner, the screw heads 60 abut annular ledges 62, as seen in FIG. 4, formed within the screw holes 50 when inserted therethrough.

Figure 3:
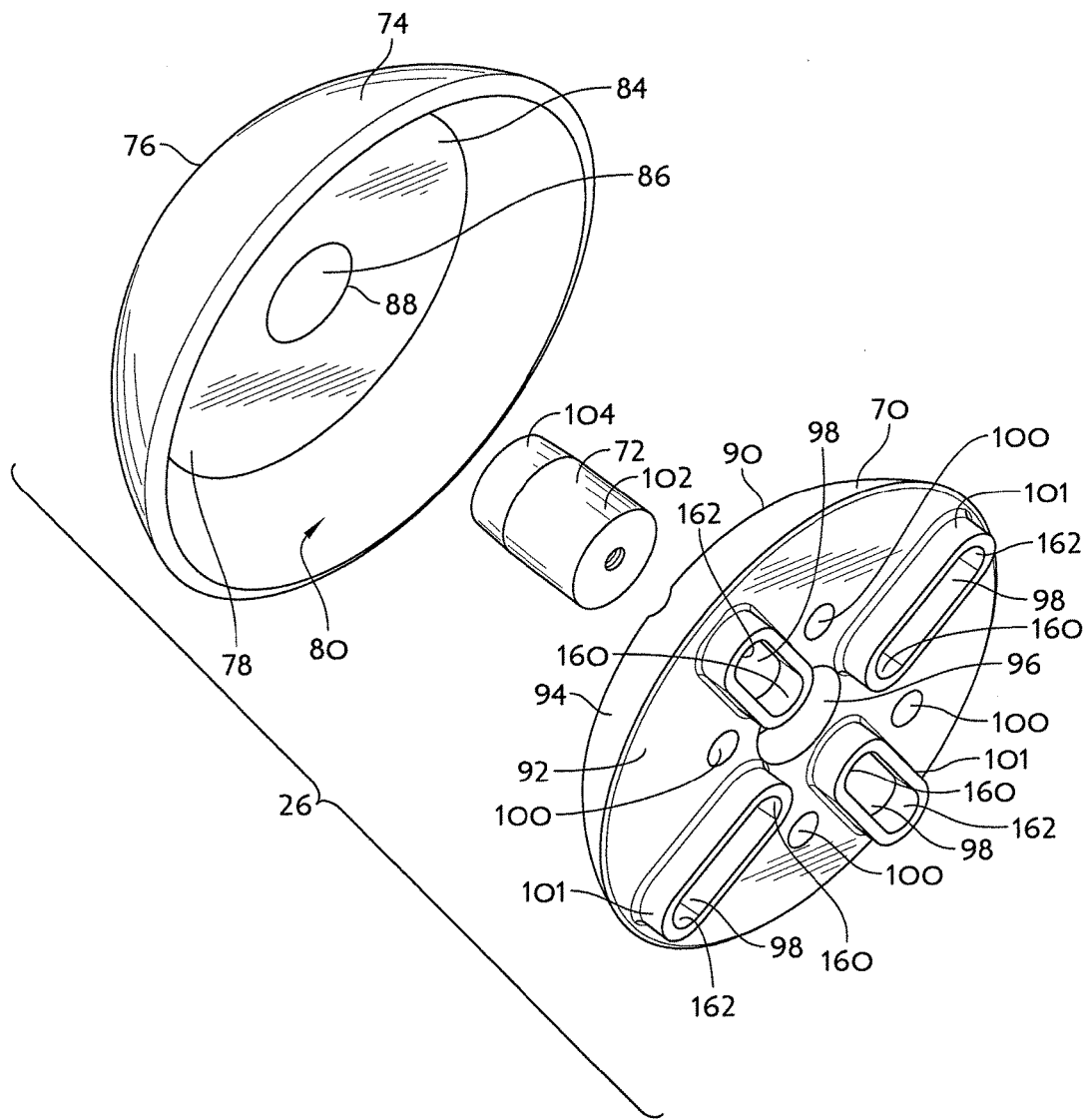
FIG. 3 is an enlarged, exploded view of the securement disk, the articulation head, and the connector of the articulation component of FIG. 2.

With reference to FIGS. 2 and 3, the articulation component 26 includes a securement disk 70, a connector 72, and an articulation head 74. The articulation head 74 includes a convex bearing surface 76 that may be defined by a portion of a sphere. The articulation head 74 further includes a reverse surface 78 defining a recess 80 for positioning of the securement disk 70 therein. In particular, the reverse surface 78 may include a partially spherical surface 82 and a planar surface 84, wherein a bore 86 is formed within the planar surface 84. The bore 86 is formed by a tapered wall 88 extending from the planar surface 84 toward the convex bearing surface 76, wherein the bore 86 terminates before reaching the convex bearing surface 76. The articulation head 74 may be constructed with biocompatible metal, such as a cobalt chrome alloy, although other materials may also be used.

The securement disk 70, as seen in FIGS. 2, 3, 5, and 6, of the articulation component 26 includes an attachment surface 90 and a securement surface 92 that are generally parallel. A partially spherical side surface 94 extends between the attachment and securement surfaces 90, 92 and may have a shape that generally conforms to a shape of the partially spherical surface 82 of the articulation head 74. The securement disk 70 may further include a central circular hole 96, four radial slots 98 spaced from the central hole 96 and extending toward the side surface 94, and four circular holes 100 having a smaller diameter than the central hole 96 and being spaced between each pair of radial slots 98. The securement disk 70 may be constructed of a porous metal, for example, titanium foam or any other suitable material.

The radial slots 98 may optionally include peripheral walls 101 extending outwardly from the securement surface 92 and surrounding the respective slots 98. In the embodiment depicted, walls forming the radial slots 98 are smooth. In an alternative embodiment, the walls forming the radial slots 98 and/or the peripheral walls 101 may include threads to facilitate insertion of the screws 24 into the radial slots 98, as will be discussed in greater detail hereinafter.

While the radial slots 98 are depicted as extending through the securement disk 70, the slots 98 may alternatively extend through only a portion of the securement disk 70. Specifically, the slots 98 need only be deep enough to provide a guide for insertion of the screws 24 into the securement disk 70.

Referring to FIGS. 2 and 3, the connector 72 is depicted as having a distal end 102 that is generally cylindrical in shape and a proximal end 104 opposite the distal end 102 and which tapers inwardly as it extends away from the distal end 102. The connector 72 may be made of rubber, a polymeric material, a metal, or any other material suitable for forming a friction fit with the articulation head 74 and the securement disk 70. In particular, during the manufacture of the articulation component 26, the securement disk 70 is secured to the articulation head 74 by the connector 72. More specifically, the securement disk 70 is molded using known molding methods. During the molding process and before the securement disk 70 has set, the distal end 102 of the connector 72 is inserted into the central circular hole 96 of the securement disk 70. As the mold sets, the securement disk 70 shrinks around the distal end 102 of the connector 72 to form a friction fit therebetween. The proximal end 104 of the connector 72 is thereafter inserted into the bore 86 of the articulation head 74 and a mallet or other tool is utilized to force the proximal end 104 of the connector 72 into the bore 86 (e.g., by exerting pressure against the securement disk 70) to form a friction fit between the connector 72 and the tapered wall 88 forming the bore 86. Optionally, these steps may be performed in any other suitable order. Still further, while one method of securing the securement disk 70 to the articulation head 74 is disclosed, any suitable manner of securing the securement disk 70 to the articulation head 74 may alternatively or additionally be utilized.

An exemplary surgical procedure for implanting the orthopaedic implant 20 of FIGS. 1 and 2 to repair a fractured humeral head 120 will now be described. It will be appreciated that details of the surgical procedure may vary, for instance, according to the preferences of the surgeon.

Figure 7:
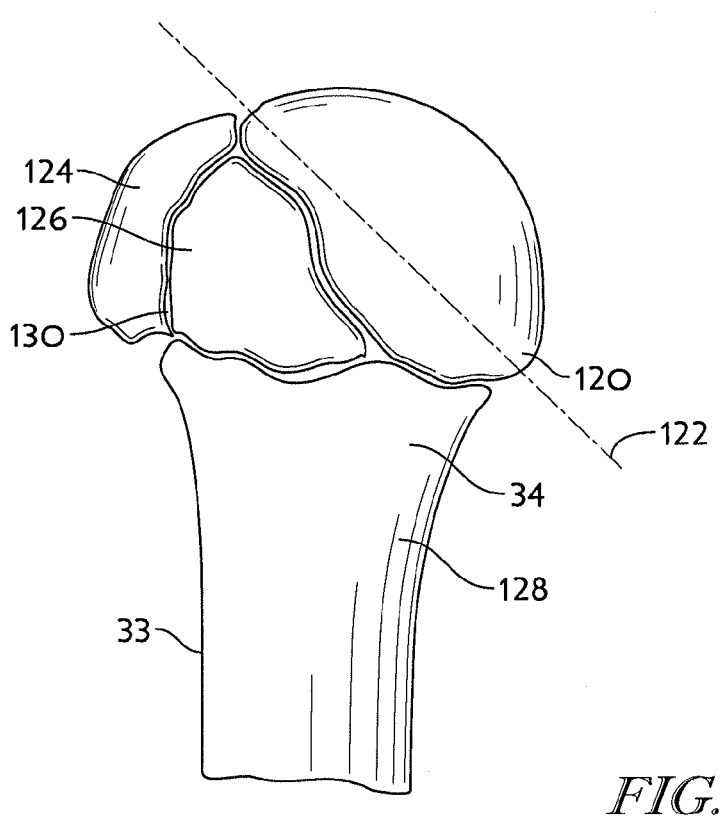
FIG. 7 is a side elevational view of a four part fracture of a proximal humerus.

When the proximal humerus 34 is fractured, the proximal humerus 34 generally breaks into several pieces, typically three or four. In particular, for a four part fracture, as illustrated in FIG. 7, the humeral head 120 splits off at the level of the anatomical neck indicated by line 122, the greater tuberosity 124 and lesser tuberosity 126 are separated from the humeral shaft 128 below the tuberosities 124, 126, and the tuberosities 124, 126 are separated from one another along the biceptal groove 130. More specifically, the greater tuberosity 124 is displaced superiorly and posteriorly by the attached rotator cuff, while the lesser tuberosity 126 is retracted medially by the attached subscapularis. The fractured end of the humeral shaft 128 is displaced medially by the pull of the pectoralis major. In a three part fracture, the greater or lesser tuberosity 124, 126 remains attached to the humeral head 120, which in consequence is rotated internally by the subscapularis tendon. Necrosis may begin for both three part and four part fractures, as there is no longer a blood supply to the humeral head 120. If this is the case, the humeral head 120 may be replaced and the greater and lesser tuberosities 124, 126 are reattached to the humeral shaft 128.

The surgeon must first gain access to the fractured humeral head 120. The patient is therefore positioned so as to allow the surgeon free access to the injured shoulder, for example, with the injured arm hanging free, thereby providing space for later manipulation of the arm. The fracture may be examined using fluoroscopy, including under internal and/or external rotation. A deltopectoral exposure may be used to identify the coracoid, acromium, and deltoid insertion. The interval between the pectoralis and the deltoid is developed and the incision line is extended distally from the coracoid. The exposure may be through a 12-14 centimeter incision. The incision may be held open using self retaining retractors. Care must be taken to identify and retract the cephalic vein. The coracobrachialis is retracted medially and the pectoralis insertion at the floor of the deltopectoral interval is located allowing the subacromial space to be developed to mobilize the proximal deltoid. While one method of accessing the fracture humeral head 120 is described, any other suitable method may be utilized.

The fixation plate 22 may be provided in multiple sizes, so an appropriately sized fixation plate 22 is selected. Thereafter, an anterior side 140 of the fixation plate 22 is aligned with the lateral surface 33 of the humeral shaft 128 and the fixation plate 22 is secured to the lateral surface 33 of the proximal humerus 34. More specifically, a bone screw 38 is inserted through the slotted screw hole 44 in the fixation plate 22 and secured to the humeral shaft 128 utilizing any tools and/or methods known in the art. The slotted screw hole 44 allows the fixation plate 22 to be moved along the humeral shaft 128 to position the fixation plate 22 appropriately. Once positioned appropriately, the bone screw 38 within the slotted screw hole 44 is tightened within the lateral surface 33. Additional bone screws 38 may be inserted through the screw holes 36 of the fixation plate 22 and secured to the humeral shaft 128 utilizing any tool known in the art. The additional bone screws 38 may be secured to the humeral shaft 128 before or after connecting the fixation plate 22 to the articulation component 36, as described below.

Any time during the procedure, the surgeon may assess whether the fracture is at a level in which repair may be possible or at a level that necessitates replacement of the fractured humeral head 120. If the surgeon believes repair is possible, he may proceed as such. For example, in a fracture wherein the humeral head 120 has not split off at the level of the anatomical neck indicated by the line 122, the humeral head 120 may not need to be replaced. In a repair, the surgeon would install the screws 24 through any number of the five screw holes 50 and the guide hole 52. During this process, the surgeon would attempt to pull the fractured bone fragments back together and anchor ends of at least some of the screws 24 in the humeral head 120, as seen in FIG. 10.

If, at any time during the installation of the screws 24, the surgeon determines that the fracture is too extensive, the surgeon may abandon the repair and easily switch to a replacement. In particular, the surgeon would use the fixation plate 22 and the screws 24 that were inserted through the screw holes 50 in the fixation plate 22 as a base for the replacement procedure. In this manner, the fixation plate 22 and the screws 24 provide a base system for both a repair and a replacement procedure and need not be removed when switching between a repair and a replacement procedure.

The orthopaedic implant 20 provides a system that allows a surgeon to begin a surgical procedure with a particular plan in mind and switch the plan intra-operatively without the need to remove the fixation plate 22 and the fasteners 24 and/or implant others. Rather, the components of the orthopaedic implant 20 may be used in different manners for a repair (e.g., using only the fixation plate 22 and the screws 24) and a replacement (e.g., using the fixation plate 22, the screws 24, and the articulation component 26).

In the replacement procedure, the detached humeral head 120 may be removed (after releasing the fractured head 120 from the greater or lesser tuberosity 124, 126 in the case of a three-part fracture). The articulation component 26 may be provided in a range of sizes that match the patient's natural humeral head. The appropriate size of articulation component 26 and screws 24 are selected to replicate the patient's natural humeral head and neck. The tuberosities 124, 126 are released from underlying soft tissues, taking care to protect the auxiliary nerve when mobilizing the lesser tuberosity and the attached subscapularis muscle tendon. The tuberosities 124, 126 are released to allow them to be coupled to each other and to the fixation plate 22.

An instrument 142, as seen in FIGS. 8A and 8B, may be used to align the fixation plate 22 with the articulation component 26. In particular, the instrument 142 may be used to set a neck length, or a distance between the fixation plate 22 and the articulation component 26, to match that of the natural anatomy of the patient. The instrument 142 includes a central shaft 144 having threading disposed therearound, an elongate projection 146 extending from a first end 148 of the central shaft 144 and having a diameter smaller than a diameter of the central shaft 144, and an enlarged head 150 extending from a second end 152 of the central shaft 144 and having a diameter larger than the diameters of the central shaft 144 and the elongate projection 146.

Referring to FIG. 8A, the elongate projection 146 is inserted through the guide hole 52 in the fixation plate 22. Simultaneously, or prior to insertion of the instrument 142, the articulation component 26 is positioned in the location of the removed humeral head 120. As the central shaft 144 reaches the guide hole 52, the threading on the central shaft 144 engages the threading of the guide hole 52, thereby requiring a user to rotate the instrument 142 to further insert the instrument 142 through the guide hole 52. The threading on the central shaft 144 and the guide hole 52 allow a surgeon to set the neck length. As the user rotates the instrument 142, the elongate projection 146 enters one of the four circular holes 100 disposed within the securement disk 70. Once the elongate projection 146 is disposed within one of the circular holes 100, the instrument 142 retains the fixation plate 22 and the articulation component 26 in alignment and prevents rotation of the articulation component 26.

Once the fixation plate 22 and the articulation component 26 are properly aligned and spaced to create the proper neck length, the screws 24 are inserted through the screw holes 50 in the fixation plate 22. The securement disk 70 of the articulation component 26 is aligned such that each of the screws 24 may be inserted into a respective radial slot 98 in the securement disk 70. If required, a drill or other tool may be used to form bores in remaining bone fragments for receiving the screws 24. Alternatively, the screws 24 may extend above the fracture line of the humeral shaft 128, or minimal bone removal may be required. As each screw 24 reaches a respective radial slot 98, the threads of the screws 24 enter the radial slots 98. Due to the porous nature of the securement disk 70, the threads of the screws 24 engage the radial slots 98 and/or the peripheral walls 101 and cut into the material of the securement disk 70. More specifically, the threads cut into the walls forming the radial slots 98 and/or the peripheral walls 101 to thereby secure the screws 24 to the securement disk 70. Since a thickness of the securement disk 70 is governed by the overall size of the articulation component 26, the peripheral walls 101 provide a greater height along which the screws 24 may engage the securement disk 70. Once the screws 24 are secured within the securement disk 70 of the articulation component 26, the instrument 142 may be removed therefrom.

While the steps of aligning the fixation plate 22 and the articulation component 26 and preventing rotation of the articulation component 26 are described and depicted herein as being accomplished using the instrument 142, the fixation plate 22 and the articulation component 26 may be alternatively or additionally aligned in any suitable manner and rotation of the articulation component 26 may be prevented in any suitable manner.

Figure 6:
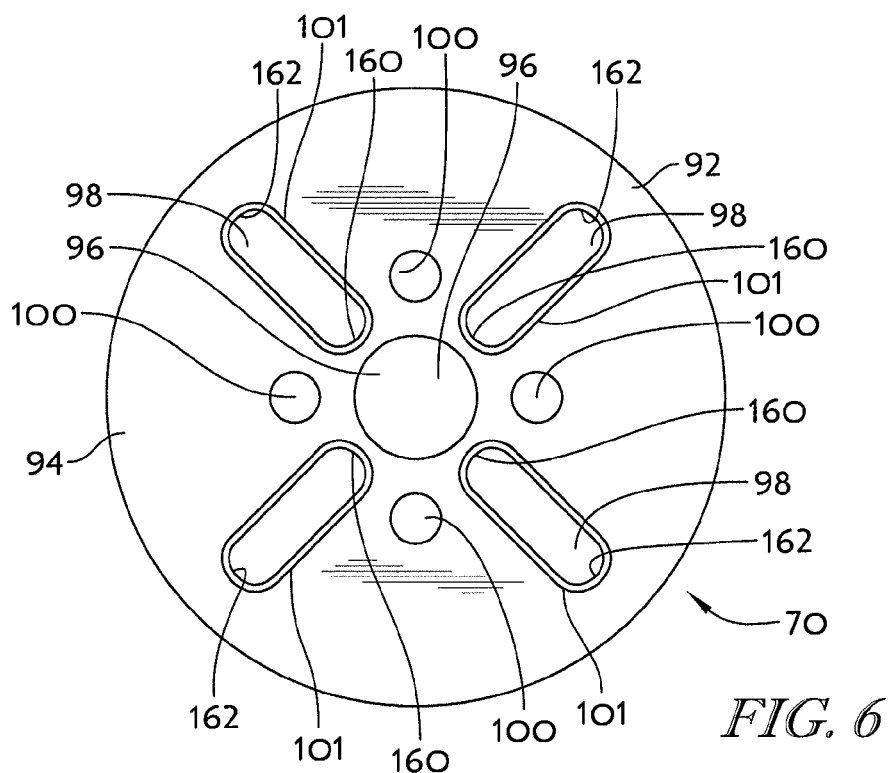

As seen in FIG. 1, the screws 24 are diverging and, thus, differently-sized screws 24 will contact the radial slots 98 at different points along the slots 98. For example, shorter screws 24 will contact the radial slots 98 closer to inner radial edges 160, as seen in FIGS. 5 and 6, of the slots 98 and longer screws 24 will contact the radial slots 98 closer to outer radial edges 162 of the slots 98. The radial slots 98 therefore allow screws 24 of different lengths to be secured to the securement disk 70 without the need for a differently-sized securement disk 70 for every length of screws 24. The surgeon selects screws that are appropriate for the patient and which create the desired neck length for that patient.

After implantation of the fixation plate 22, the articulation component 26, and the screws 24, bone fragments, such as the greater and lesser tuberosities 124, 126 may be attached in any suitable manner to the humeral shaft 128 to position and prevent movement of the bone fragments.

While screws are described herein as securing or implanting one or more components to each other and/or to bone, any suitable fasteners may be used.

While the embodiments of the present disclosure are described with respect to implantation upon and within a humerus, the principles of the present invention may be utilized in conjunction with other implants, for example for the hip and/or the knee.

As will become apparent from reading the present specification, any of the features of any of the embodiments disclosed herein may be incorporated within any of the other embodiments without departing from the scope of the present disclosure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic implant, comprising:
    an articulation head comprising a bearing surface and a reverse surface; and
    a securement disk comprising:
    an attachment surface attached to at least a portion of the reverse surface of the articulation head;
    a securement surface opposite the attachment surface and adapted for coupling to a fixation plate secured to a bone;
    a central aperture extending through the attachment surface and the securement surface; and
    a plurality of elongated openings arranged circumferentially around the central aperture, each elongated opening being formed in the securement surface of the securement disk and adapted to accept a fastener therein to couple the fixation plate to the attachment surface;
    wherein each elongated opening extends in a radial direction away from the central aperture, and the securement disk comprises a porous material.

2. The implant of claim 1, wherein a shorter fastener is secured within the elongated opening near an inner edge of the elongated opening and a longer fastener is secured within the elongated opening near an outer edge of the elongated opening, thereby allowing flexibility in the length of fasteners used with the articulation component.

3. The implant of claim 1, wherein each elongated opening extend into the securement disk between the securement surface and the attachment surface.

4. The implant of claim 1, wherein each elongated opening includes at least one wall along extending outwardly from at least a portion of a perimeter of each elongated opening, wherein each fastener engages the at least one wall and a wall forming each elongated opening to retain the fastener within the slot.

5. The implant of claim 1, wherein the securement disk is formed of titanium foam.

* * * * *